(12) United States Patent
Cuckler et al.

(10) Patent No.: US 7,364,580 B2
(45) Date of Patent: Apr. 29, 2008

(54) BONE-CUTTING APPARATUS

(75) Inventors: John M Cuckler, Birmingham, AL (US); Robert Metzger, Wakarusa, IN (US); Kurt Schmidt, Lafayette, IN (US); Trevor S Schlueter, Leesburg, IN (US); James M McKale, Syracuse, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 569 days.

(21) Appl. No.: 10/680,902

(22) Filed: Oct. 8, 2003

(65) Prior Publication Data

US 2005/0080424 A1 Apr. 14, 2005

(51) Int. Cl.
*A61B 17/00* (2006.01)
(52) U.S. Cl. .................................................. 606/79
(58) Field of Classification Search ............... 606/79, 606/86, 87, 88, 89
See application file for complete search history.

(56) References Cited

U.S. PATENT DOCUMENTS

| | | | |
|---|---|---|---|
| 5,047,032 A | 9/1991 | Jellicoe | |
| 5,047,033 A | 9/1991 | Fallin | |
| 5,304,181 A | 4/1994 | Caspari et al. | |
| 5,415,662 A | 5/1995 | Ferrante et al. | |
| 5,496,324 A * | 3/1996 | Barnes | 606/79 |
| 5,591,207 A * | 1/1997 | Coleman | 606/232 |
| 5,593,411 A | 1/1997 | Stalcup et al. | |
| 5,653,714 A * | 8/1997 | Dietz et al. | 606/87 |
| 5,769,854 A * | 6/1998 | Bastian et al. | 606/88 |
| 5,810,829 A | 9/1998 | Elliott et al. | |
| 5,935,132 A | 8/1999 | Bettuchi et al. | |
| 5,957,925 A | 9/1999 | Cook et al. | |
| 6,106,292 A * | 8/2000 | Hollander et al. | 433/165 |
| 6,258,095 B1 * | 7/2001 | Lombardo et al. | 606/88 |

FOREIGN PATENT DOCUMENTS

DE 203 03 643 7/2003

* cited by examiner

*Primary Examiner*—Eduardo C. Robert
*Assistant Examiner*—James L Swiger
(74) *Attorney, Agent, or Firm*—Harness, Dickey & Pierce, P.L.C.

(57) ABSTRACT

A bone-cutting apparatus and associated method and system. In one embodiment, the apparatus includes a guide removably attachable to a bone, and a rotatable mill coupled to the guide. The guide has a box-cut opening and the mill is pivotable within the opening. In one embodiment, the mill is laterally adjustable relative to the opening.

12 Claims, 6 Drawing Sheets

BONE-CUTTING APPARATUS

FIELD OF THE INVENTION

The present invention relates to a bone-cutting apparatus and associated method.

BACKGROUND OF THE INVENTION

Healthy knee joints include two cruciate ligaments, the anterior cruciate ligament (ACL) and the posterior cruciate ligament (PCL). The ACL is often damaged in diseased or injured knee joints, and is may be removed during total knee replacement. It is considered desirable, however, to retain the PCL because of its importance for the stability of the knee during bending. When the PCL is damaged beyond repair or otherwise must be removed, a posterior stabilized knee prosthesis is implanted. This prosthesis includes a femoral component with an intercondylar box-shaped part. Therefore, a similarly box-shaped intercondylar bone portion must be resected from the femur to accommodate the femoral component.

Knee joints that require posterior stabilized knee prosthesis are typically severely damaged and intercondylar box resection is a challenging and painstaking procedure. Several guides and milling devices have been developed to assist the surgeon in this procedure, which often requires an impacting force to remove the intercondylar bone after a number of resections have been made. Nevertheless, a bone-cutting device that is easy of use, reasonably fast and avoids impact is still desirable.

SUMMARY OF THE INVENTION

One embodiment of the invention provides a bone-cutting apparatus that includes a guide and a rotatable mill that is coupled to the guide. The guide is removably attachable to a bone and has a box-cut opening. The mill is pivotable within the opening along a cutting plane between a first position, in which the mill is laterally adjustable relative to the opening, and a second position, in which the mill is laterally constrained relative to the opening.

In another embodiment, the bone-cutting apparatus includes a rotatable mill and a guide. The guide has a base, a flange, two guiding sides, and a box-cut opening. The apparatus also includes a rod that is rotatably supported on the base and has a plurality of truncated grooves. A pin is attached to the base and selectively engages one of the grooves. The mill is coupled to the rod and is movable between a first position, in which the mill is substantially parallel to the base, and a last position, in which the mill is at an angle relative to the base. The mill is laterally adjustable within the opening in the first position. When the mill is between the first and the last positions, the pin engages one of the grooves and the mill is laterally constrained.

Another embodiment of the invention provides a bone-cutting apparatus that has a guide removably attachable to a bone and a rotatable mill coupled to the guide. The mill is pivotable within an opening of the guide. In one embodiment, the opening is box-shaped and the mill pivots within the opening along a plurality of parallel planes that are perpendicular to a lateral axis along which the mill can be shifted.

In another embodiment, the bone-cutting apparatus includes a guide removably attachable to a bone and a rotatable mill coupled to the guide. The guide has a base, a bone-attachment flange substantially parallel to the base, and two guiding sides. The guiding sides are perpendicular to the base. The mill is pivotable within an opening of the guide. In one embodiment, the mill pivots within the opening along a plurality of parallel planes that are perpendicular to a lateral axis.

Another embodiment of the invention provides a knee system including a femoral component having an intercondylar box, and a cutter for removing an intercondylar bone portion from a distal end of a femoral bone for receiving the intercondylar box. The cutter includes a guide defining an opening, and a rotatable mill coupled to the guide. The mill is pivotable within the opening to cut the intercondylar bone portion.

Another embodiment provides a method for performing a box resection of a bone. The method includes attaching a guide to the bone, pivoting a rotatable mill that is coupled to the guide, and forming the box resection with the mill. The method may also include inserting an intercondylar box of a femoral component into the box resection formed in the bone. In another embodiment, the method includes selectively shifting the mill to a lateral location within a box-cut opening of the guide, and pivoting the mill. Shifting and pivoting may be repeated until the box resection is completed.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF VARIOUS EMBODIMENTS

The following description of various embodiments is merely exemplary in nature and is in no way intended to limit the invention, its application, or uses.

Figure 1:
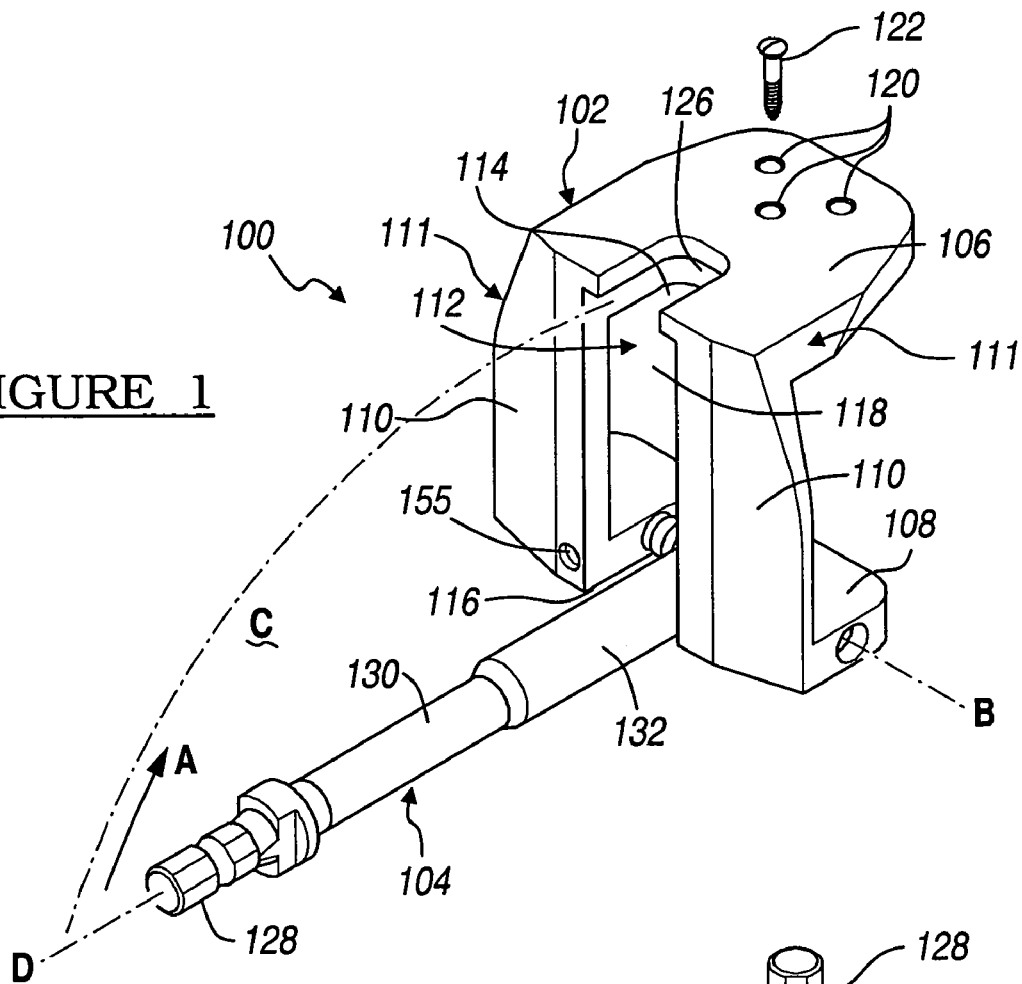
FIG. 1 is a perspective view of an embodiment of the bone cutting apparatus of the present invention, shown in a first position.

Referring to FIG. 1, an embodiment of a bone-cutting apparatus 100 according the present invention is shown. The apparatus includes a guide 102 and a mill or reamer or similar cutting tool 104 that can rotate about its own longitudinal axis "D". The guide 102 may be a generally U-shaped member that includes a flange 106 and a base 108. The flange 106 and the base 108 are joined by a pair of guiding sides 110, which are substantially orthogonal to the flange 106 and the base 108. The guide 102 includes a generally "box-cut" shaped opening 112, which is defined by a U-shaped flange cutout 114, a U-shaped base cutout 116 and a rectangular spacing 118 between the guiding sides 110. The box-cut opening 112 is substantially sized and shaped to conform to the amount of bone that must be removed from a bone before inserting a portion of a prosthesis component. For example, in a posterior stabilized knee prosthesis, the opening 112 is sized for the removal of intercondylar bone which is necessary for the insertion of an intercondylar box 97 of the prosthesis. In the following description, the bone-cutting apparatus 100, is described in reference to posterior stabilized knee prosthesis for the sake of clarity, but it is should be appreciated that the apparatus 100 is not restricted to such use.

Figure 4:
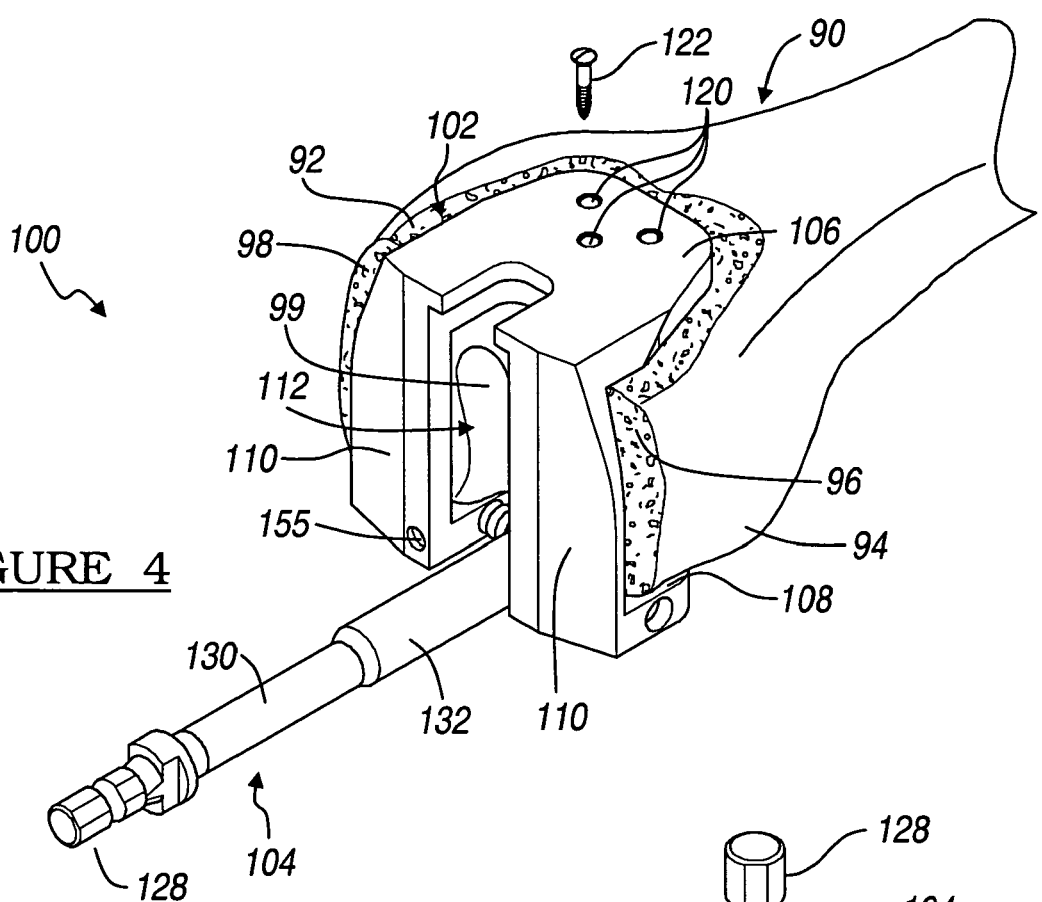
FIG. 4 is an environmental view of the embodiment of FIG. 1.

The flange 106 may include a plurality of holes 120 for securing the apparatus 100 to a bone using suitable removable fasteners 122, such as bone nails, drill bits, pins, etc. In a posterior stabilized knee prosthesis, for example, the apparatus 100 is used on the resected distal femur 90, as shown in FIG. 4. The flange 106 is placed on the resected anterior surface 92 and secured thereon with the fasteners 122. The base 108 is placed under the resected posterior surface 94, such that the guiding sides 110 are in front of the resected medial and lateral condyles 96, 98, shown for a right knee in FIG. 4. In this position, the opening 112 of the guide 102 may be aligned to remove an intercondylar bone portion 99.

Figure 2:
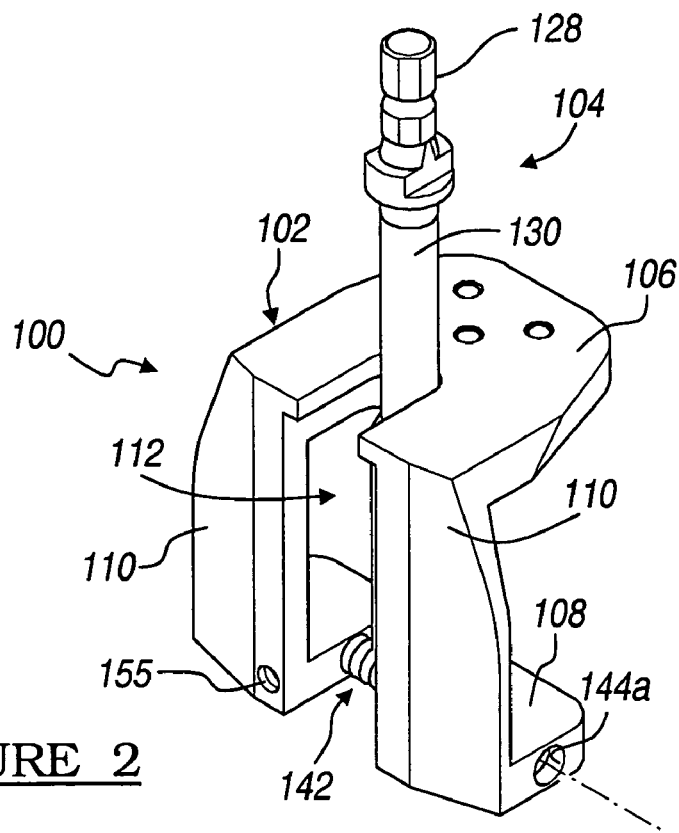
FIG. 2 is a perspective view of an embodiment of the bone cutting apparatus of the present invention, shown in a second position and a first lateral location.
Figure 3:
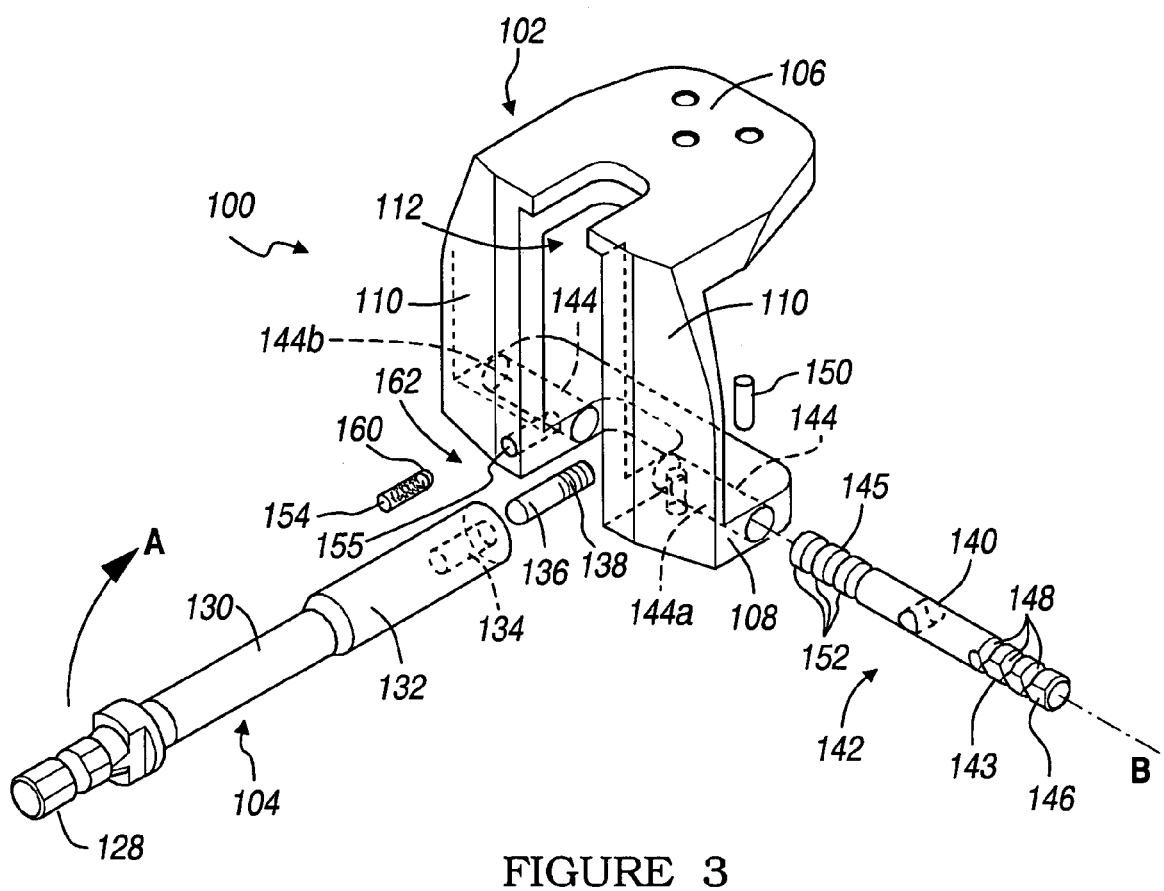
FIG. 3 is an exploded perspective view of an embodiment of the bone cutting apparatus of the present invention, shown in the first position.

The mill 104 is pivotably connected to the guide 102, such that it can rotate in the direction of an arrow "A" toward the flange 106 from a first position, shown in FIG. 1 to a last position shown in FIG. 2, and any position intermediate the first and the last positions. The term "second position" as used herein includes the last position and all the positions that span the interval between the first position and the last position in the direction of the arrow A. In the first position, the mill 104 is substantially coplanar or parallel to the base 108 and it can move laterally along a lateral axis "B". In the last position, the mill 104 is prevented from rotating further in the direction of the arrow A by a stopping wall 126 of the flange cutout 114. For a posterior stabilized knee prosthesis, the mill 104 is adjacent to the posterior surface 94 in the first position, and adjacent to the anterior surface 92 in the last position. The angle between the first and last positions is substantially 90° for a posterior stabilized knee prosthesis, but other angles less or greater than 90° may be provided by changing the depth of the flange cutout 114 or the angle of the guiding sides 110 with the flange 106 for other applications that do not require resection of rectangular bone portions.

Figure 5:
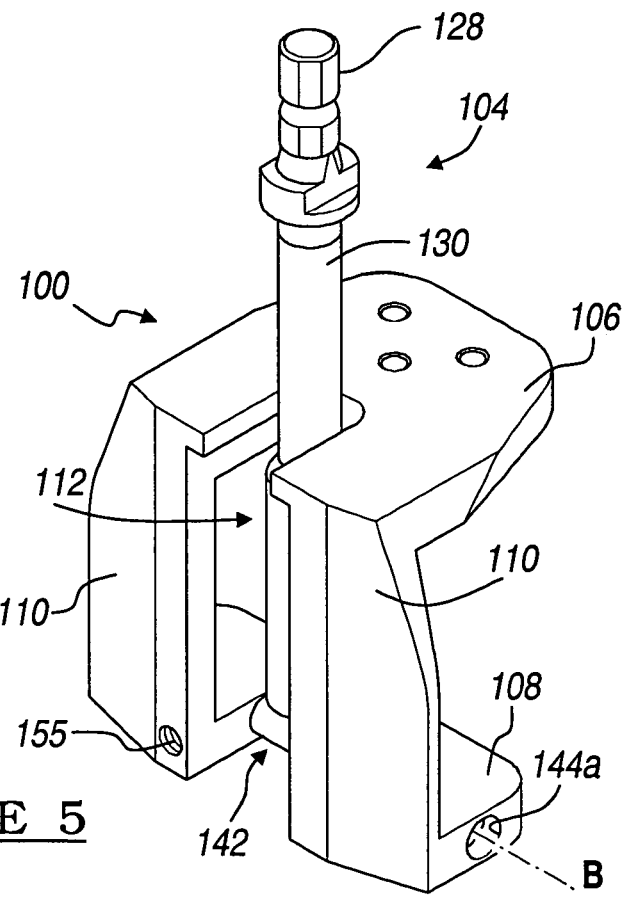
FIG. 5 is the embodiment of FIG. 2, shown in a second position and a second lateral location.

Referring to FIG. 5, the mill 104 includes a driven end 128, which may be connected to a spindle for power driven rotation or to a crank handle for manual rotation, and a shaft 130 with a cutting portion 132. The cutting portion 132 includes a bore 134 which rotatably receives a pivot pin 136. The pivot pin 136 has a threaded end 138 that engages with a center slot 140 in a rod 142. The rod 142 is sized to be received in two halves 144a, 144b of a split bore 144 in the base 108, and is oriented coaxially with the lateral axis B.

The rod 142 may be moved along the lateral axis B to allow lateral repositioning of the mill 104 relative to the box-cut opening 112. In one embodiment, the rod 142 slides within the bore 110, such that the mill 104 is easily repositioned by manually shifting the shaft 130 laterally, i.e. in a direction parallel to the lateral axis B, thereby causing the rod 142 to slide within the bore 110. It will be appreciated that in some other applications, it may be desirable to control the lateral movement of the mill 104 by controlling the movement of the rod 142, such as, for example, by providing for threaded engagement between a portion of the rod 142 and a portion of the bore 110 and advancing the rod 142 using a tool such as a screwdriver or socket at one end of the rod 142, or other means within the purview of an artisan of ordinary skill.

In one embodiment, to better stabilize the mill 104 during cutting, lateral movement and repositioning of mill 104 is only permitted when the mill 104 is in the first position, in which no cutting occurs. When the mill 104 is pivoted toward the flange 106, lateral movement of the mill 104 may be prevented by preventing lateral movement of the rod 142. Thus, during pivoting, the mill 104 may be constrained to remain on a single cutting plane "C", i.e. on a plane that is perpendicular to the lateral axis B. Such lateral constraint may not be necessary for certain applications.

In one embodiment, the rod 142 may include one or more grooves 148 located at predetermined intervals along a first portion 143 of the rod 142. The grooves 148 are positioned such that one of them can selectively capture a pin 150 when the mill 104 is pivoted in the direction of the arrow A. The pin 150 is attached substantially perpendicularly to the base 108 and traverses the first half 144a of the bore 144. When the pin 150 is captured by one of the grooves 148, it prevents any lateral movement of the rod 142, thus stabilizing the lateral position of the mill 104 during cutting. The grooves 148 are truncated, i.e. they do not extend over the entire circumference of the rod 142, terminating at a chamfered portion 146 of the rod 142, which is oriented relative to the center slot 140 such that the pin 150 is not captured by any of the grooves 144, when the mill 104 is in the first position. When the mill 104 is pivoted about the lateral axis B, the rod 142 rotates about the same axis such that one of the grooves 144 captures the pin 150.

The rod 142 may include a set of detents 152 located on a second portion 145 of the rod 142. The first and second portions 143, 145 of the rod 142 are on opposite sides of the center slot 140 and are received within the respective halves 144a, 144b of the split bore 144. The detents 152 may extend over the entire circumference of the rod 142. A commercially available spring-loaded ball plunger 154 may be inserted in a hole 155 of the base 108 to selectively engage one of the detents 152. The detents 152 are placed at locations symmetric to the locations of the grooves 148 about the center slot 140, such that a desired lateral location for the mill 104 may be easily selected by moving the mill 104 laterally, while in the first position, until the ball 160 of the ball plunger 154 snaps into the appropriate detent 152. The ball plunger 154 and the detents 152, in cooperation with the grooves 148 and the pin 150, define an indexing mechanism 162 for quick lateral positioning and repositioning of the mill 104.

In one embodiment, there are three grooves 148 corresponding to three lateral locations of the mill 104 in relation to the opening 112, such that operation of the mill 104 in each lateral location removes one third (⅓) of the intercondylar bone 99. Two of these lateral locations are illustrated in FIGS. 2 and 5, in which the mill 104 has been pivoted to the last position. Depending on the quality/ strength characteristics of the bone and the size of the bone 90 in the lateral dimension, i.e. the dimension along the lateral axis B and the size of the cutting portion 132 of the mill 104, a smaller or greater number of grooves 148 may be used. For fragile or damaged bone, for example, it may be desirable to use a greater number of smaller width cuts, in which case the rod 142 is provided with greater number of grooves 148 delineating a corresponding number of lateral locations.

Figure 6:
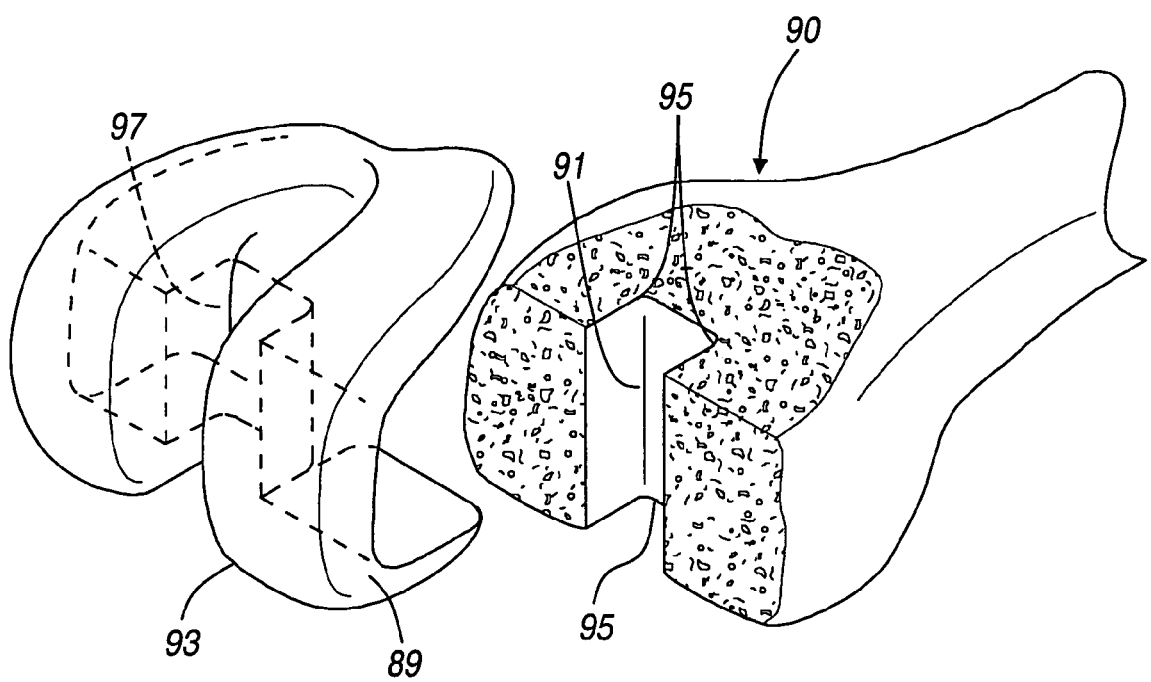
FIG. 6 is an exploded view of a portion of a distal femur prepared to receive a femoral component according to an embodiment of the present invention.
Figure 7:
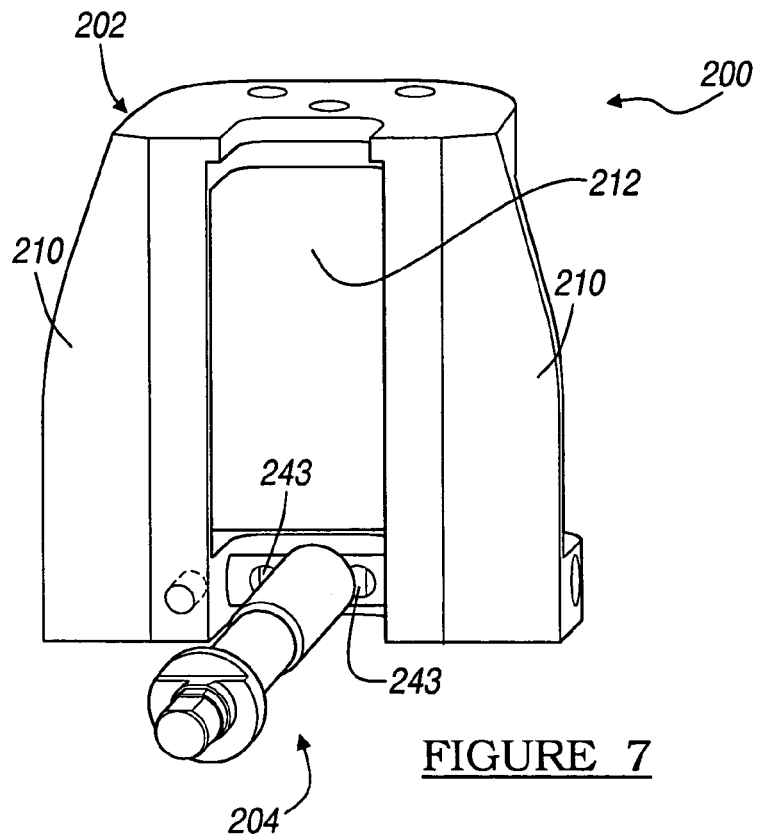
FIG. 7 is a perspective view of an embodiment of the bone cutting apparatus of the present invention, shown in a first position.
Figure 8:
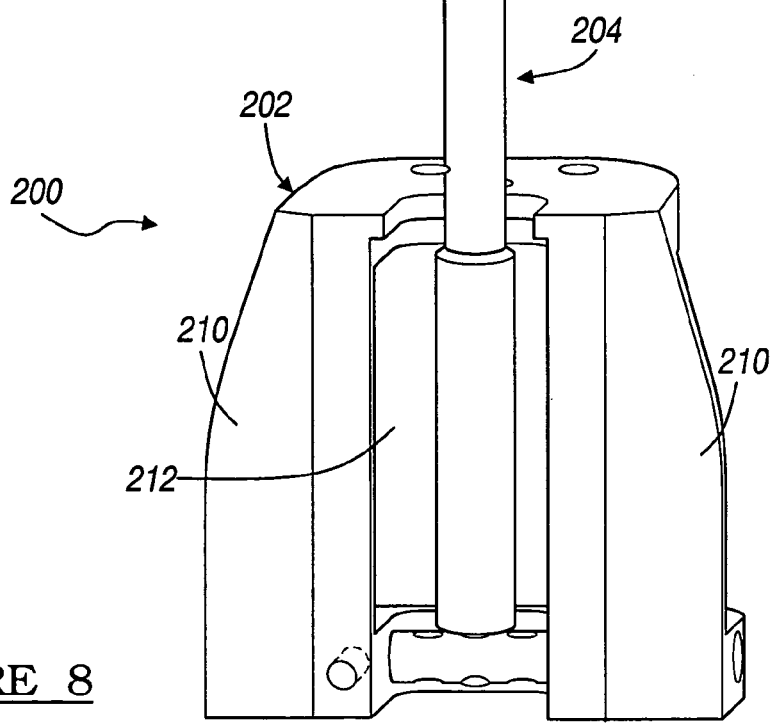
FIG. 8 is a perspective view of the bone cutting apparatus of FIG. 7, shown in a second position.
Figure 9:
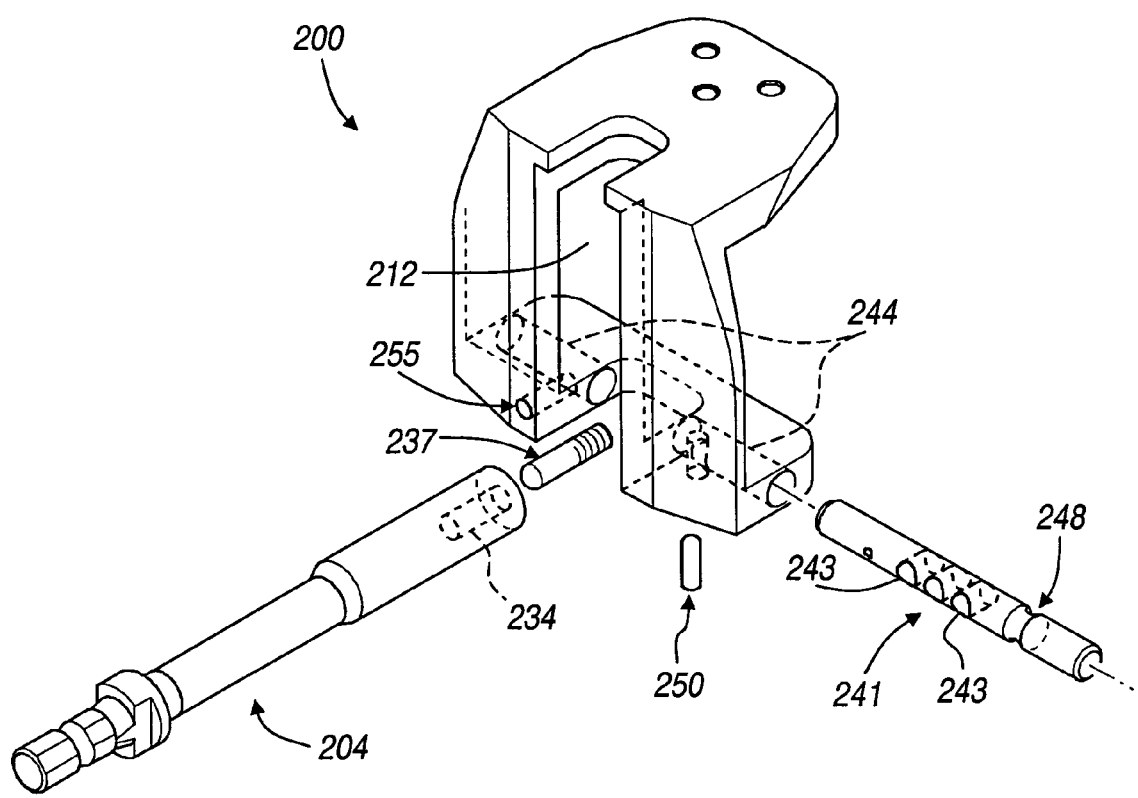
FIG. 9 is an exploded view of the bone cutting apparatus of FIG. 7.

Similarly, it will be appreciated that the number of lateral shifts of the mill 104 that are required for the removal of the bone portion 99 depends on the width of the bone portion 99 relative to the diameter of the cutting portion 132 of the mill 104. Therefore, it is also possible to remove the entire bone portion 99 with single pass of the mill 104, that is without need for any lateral shifting, if the diameter of the mill 104 substantially conforms to the size of the bone portion 99. After the bone portion 99 is removed, a box-like cavity 91 with rounded corners 95 is defined in the bone 90 for receiving a femoral component 93, as shown in FIG. 6. When a small-diameter mill 104 is used, the corners 95 of the cavity 91 will have a smaller radius as compared to when a bigger diameter mill 104 is used. If right-angle corners are desired in a particular application, the surgeon could chisel the corners 95 of the cavity 91 to form right-angle corners 95. The guide 102 has two lateral surfaces 111, which are shaped similarly to corresponding lateral sides 89 of the femoral component 93 to aid in positioning the guide 102.

In operation, the bone-cutting apparatus 100 is attached to the resected bone 90 by inserting the bone 90 between the flange 106 and the base 108, such that the volume of the bone portion 99 to be removed is framed by the box-cut opening 112 of the apparatus 100. The apparatus 100 is then secured by attaching the flange 106 to the bone 90 with fasteners 122. Starting from the first position, the mill 104 is moved along the lateral axis B to a first lateral location while at the first position. The mill 104 is then rotated (spinned) manually or by power, and is also pivoted from the first position to a second position, while remaining locked in the first lateral location and cutting through a segment of bone portion 99. Next, the mill 104 is returned to the first position and is shifted to a second lateral location along the lateral axis B, while in the first position. The shifting, pivoting and cutting process is repeated as necessary until the entire bone portion 99 is removed. During this procedure, selecting each of the lateral locations, i.e. moving the mill 104 from one to another cutting plane C, may be facilitated by the indexing mechanism 162.

Another embodiment of the bone cutting apparatus 200 is illustrated in FIGS. 7-11. Elements common to embodiments 100 and 200 are referenced with numerals having the same second and third digits and prefaced by the digit 1 or 2 respectively, such as for example, the mill 104, 204. The description of elements common to both embodiments will not be repeated. In this embodiment, the rod 242 includes one groove 248 that captures the pin 250 to prevent lateral movement of the rod 242. The rod 242 includes a center hole 241 and two side holes 243, corresponding to the medial and lateral positions. To make a cut in the lateral or medial position, the mill 204 is removed from the center hole 241 of the rod 242 and is inserted in one of the side holes 243. To facilitate the engagement and disengagement of the mill 204 to and from the rod 142, the mill 204 includes a press-fit guide pin 237 which snaps inside one of the three holes 241, 243 and rotates with the mill 204.

The various embodiments of the bone-cutting apparatus 100, 200 provide a convenient cutting tool, which can guide and resect a portion of a bone, such as an intercondylar box portion, for example, quickly and precisely. By providing a pivotable mill, which can also be selectively shifted in a lateral direction, the intercondylar box portion can be removed without the need to apply any impact forces. The bone-cutting apparatus 100, 200 may be an important component of a knee replacement system that includes femoral components 93, such as those used for posterior stabilized knee prosthesis.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A bone-cutting apparatus comprising:
   a guide removably attachable to a bone, the guide defining a box-cut opening;
   a rotatable mill coupled to the guide, wherein the mill is pivotable within the opening along a cutting plane between a first position, in which the mill is laterally adjustable relative to the opening, and a second position, in which the mill is laterally constrained relative to the opening, the second position including a sequence of positions from the first position toward a last position, wherein the last position is determined by a wall of the guide; and
   a rod rotatably supported by the guide and connected with the mill,
   wherein the rod includes a center hole and two side holes for selectively receiving the mill.

2. The apparatus of claim 1, wherein the mill is coupled to one of the holes by a press-fit guide pin.

3. The apparatus of claim 1, further comprising a pin supported on the guide engaging a groove in the rod to prevent lateral sliding of the rod relative to the base.

4. The apparatus of claim 1, wherein the rod is prevented from sliding when the mill is in the second position.

5. The apparatus of claim 4, further comprising a pin supported on the guide, and wherein the rod includes a plurality of truncated grooves, such that the pin is selectively engaged in one of the grooves when the mill is pivoted from the first to the second position.

6. A bone-cutting apparatus comprising:
   a guide having a base, a bone-attachment flange substantially parallel to the base and two guiding sides substantially perpendicular to the base, the guide defining a box-cut opening having a lateral axis substantially parallel to the flange and extending substantially perpendicularly between the two guiding sides;
   a rod rotatably supported by the base substantially perpendicularly to the lateral axis, wherein a first portion of the rod includes a plurality of truncated grooves;
   a pin attached to the base substantially perpendicularly to the base and selectively engaging one of the grooves; and
   a rotatable mill coupled to the rod and pivotable about the lateral axis between a first position, in which the mill is substantially parallel to the base, and a last position, in which the mill is at an angle relative to the base, wherein the mill is slidably adjustable along the lateral axis within the opening in the first position, and wherein, when the mill is between the first and the last positions, the pin engages one of the grooves and the mill is substantially fixed relative to the lateral axis.

7. A bone-cutting apparatus comprising:
a guide having a base, a bone-attachment flange and two guiding sides, the guide defining a box-cut opening;
a rod rotatably supported by the base, wherein a first portion of the rod includes a plurality of truncated grooves, wherein the rod is rotatably received in a split bore within the base;
a pin attached to the base and selectively engaging one of the grooves; and
a rotatable mill coupled to the rod and movable between a first position, in which the mill is substantially parallel to the base, and a last position, in which the mill is at an angle relative to the base, wherein the mill is laterally adjustable within the opening in the first position, and
wherein, when the mill is between the first and the last positions, the pin engages one of the grooves and the mill is laterally constrained.

8. The apparatus of claim 7, wherein the pin traverses a first portion of the bore.

9. The apparatus of claim 8, wherein the rod has a chamfered portion preventing engagement of the pin with the grooves when the mill is in the first position.

10. The apparatus of claim 7, further comprising an indexing mechanism for selecting a lateral location of the mill in the first position.

11. The apparatus of claim 10, wherein the indexing mechanism includes a spring-loaded ball plunger and a plurality of detents on a second portion of the rod.

12. The apparatus of claim 7, wherein the mill includes a shaft having a driven end, a cutting portion, and a bore rotatably receiving a pivot pin having an end threadably engaging the rod.

* * * * *

UNITED STATES PATENT AND TRADEMARK OFFICE
CERTIFICATE OF CORRECTION

PATENT NO. : 7,364,580 B2  
APPLICATION NO. : 10/680902  
DATED : April 29, 2008  
INVENTOR(S) : John M. Cuckler et al.

It is certified that error appears in the above-identified patent and that said Letters Patent is hereby corrected as shown below:

Column 1  
Line 13, delete "is".  
Line 23-24, "prosthesis" should be --prostheses--.  
Line 30, "of" should be --to--.

Column 3  
Line 2, insert --to-- after "according".  
Line 20, insert --a-- before "posterior".  
Line 21, delete "is".

Signed and Sealed this

Fourteenth Day of October, 2008

JON W. DUDAS  
*Director of the United States Patent and Trademark Office*